(12) United States Patent  
Ortiz et al.

(10) Patent No.: US 7,651,017 B2
(45) Date of Patent: Jan. 26, 2010

(54) SURGICAL STAPLER WITH A BENDABLE END EFFECTOR

(75) Inventors: Mark S. Ortiz, Milford, OH (US); Michael Stokes, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 421 days.

(21) Appl. No.: 11/287,525

(22) Filed: Nov. 23, 2005

(65) Prior Publication Data
US 2007/0114261 A1    May 24, 2007

(51) Int. Cl.
*A61B 17/068* (2006.01)

(52) U.S. Cl. .................. 227/176.1; 227/19; 606/219

(58) Field of Classification Search ............. 227/176.1, 227/175.1, 19, 180.1, 179.1; 606/139, 219
See application file for complete search history.

(56) References Cited

U.S. PATENT DOCUMENTS

| | | | |
|---|---|---|---|
| 2,004,013 A | 6/1935 | Reed | |
| 2,004,014 A | 6/1935 | Sanford | |
| 2,004,172 A | 6/1935 | Sanford | |
| 4,473,077 A | 9/1984 | Noiles et al. | |
| 4,566,620 A * | 1/1986 | Green et al. | 227/19 |
| 4,610,383 A * | 9/1986 | Rothfuss et al. | 227/19 |
| 4,728,020 A | 3/1988 | Green et al. | |
| 4,754,909 A | 7/1988 | Barker et al. | |
| 4,841,888 A | 6/1989 | Mills et al. | |
| 4,869,414 A | 9/1989 | Green et al. | |
| 5,041,129 A | 8/1991 | Hayhurst et al. | |
| 5,042,707 A * | 8/1991 | Taheri | 606/213 |
| 5,080,663 A | 1/1992 | Mills et al. | |
| 5,217,486 A | 6/1993 | Rice et al. | |
| 5,269,809 A | 12/1993 | Hayhurst et al. | |
| 5,271,543 A | 12/1993 | Grant et al. | |
| 5,312,023 A | 5/1994 | Green et al. | |
| 5,326,013 A | 7/1994 | Green et al. | |
| 5,330,486 A | 7/1994 | Wilk | |
| 5,330,502 A | 7/1994 | Hassler et al. | |

(Continued)

FOREIGN PATENT DOCUMENTS

EP      0 832 605 A1     4/1998

(Continued)

OTHER PUBLICATIONS

Communication from corresponding EP Application No. 06255973.7, dated Mar. 21, 2007.

*Primary Examiner*—Scott A. Smith
(74) *Attorney, Agent, or Firm*—Nutter McClennen & Fish LLP (57) ABSTRACT

A surgical stapler having a selectively bendable end effector is provided. A staple holding jaw of the end effector is coupled to another jaw for grasping tissue to be stapled. The stapler can adapted to drive staples into tissue having a pattern conforming with the selected shape of the end effector. In particular, the end effector can be adapted to drive staples in a linear pattern when the end effector orients staples in a substantially linear configuration. The end effector can also be adapted to drive staples in a non linear pattern when the end effector orients staples in a non linear configuration. Methods of stapling tissue with a stapler having a bendable end effector are also discussed.

20 Claims, 11 Drawing Sheets

U.S. PATENT DOCUMENTS

| | | | |
|---|---|---|---|
| 5,348,259 A | 9/1994 | Blanco et al. | |
| 5,374,277 A | 12/1994 | Hassler | |
| 5,376,101 A | 12/1994 | Green et al. | |
| 5,379,933 A | 1/1995 | Green et al. | |
| 5,381,943 A | 1/1995 | Allen et al. | |
| 5,383,888 A | 1/1995 | Zvenyatsky et al. | |
| 5,398,670 A | 3/1995 | Ortiz et al. | |
| 5,403,342 A | 4/1995 | Tovey et al. | |
| 5,405,073 A | 4/1995 | Porter | |
| 5,405,344 A | 4/1995 | Williamson et al. | |
| 5,409,498 A | 4/1995 | Braddock et al. | |
| 5,411,519 A | 5/1995 | Tovey et al. | |
| 5,417,203 A | 5/1995 | Tovey et al. | |
| 5,437,681 A | 8/1995 | Meade et al. | |
| 5,456,684 A | 10/1995 | Schmidt et al. | |
| 5,462,558 A | 10/1995 | Kolesa et al. | |
| 5,482,197 A * | 1/1996 | Green et al. | 227/178.1 |
| 5,507,776 A | 4/1996 | Hempel | |
| 5,514,159 A | 5/1996 | Matula et al. | |
| 5,540,705 A | 7/1996 | Meade et al. | |
| 5,571,119 A | 11/1996 | Atala | |
| 5,584,861 A | 12/1996 | Swain et al. | |
| 5,607,094 A | 3/1997 | Clark et al. | |
| 5,626,607 A * | 5/1997 | Malecki et al. | 606/205 |
| 5,680,982 A * | 10/1997 | Schulze et al. | 227/175.1 |
| 5,690,269 A * | 11/1997 | Bolanos et al. | 227/176.1 |
| 5,704,534 A * | 1/1998 | Huitema et al. | 227/175.1 |
| 5,709,693 A | 1/1998 | Taylor | |
| 5,713,910 A | 2/1998 | Gordon et al. | |
| 5,749,893 A * | 5/1998 | Vidal et al. | 606/205 |
| 5,755,730 A | 5/1998 | Swain et al. | |
| 5,814,071 A | 9/1998 | McDevitt et al. | |
| 5,833,695 A * | 11/1998 | Yoon | 606/139 |
| 5,860,992 A | 1/1999 | Daniel et al. | |
| 5,865,361 A * | 2/1999 | Milliman et al. | 227/176.1 |
| 5,887,594 A | 3/1999 | LoCicero, III | |
| 5,899,921 A | 5/1999 | Caspari et al. | |
| 5,901,895 A * | 5/1999 | Heaton et al. | 227/176.1 |
| 5,902,321 A | 5/1999 | Caspari et al. | |
| 6,010,515 A | 1/2000 | Swain et al. | |
| 6,036,694 A | 3/2000 | Goble et al. | |
| 6,200,329 B1 | 3/2001 | Fung et al. | |
| 6,241,139 B1 * | 6/2001 | Milliman et al. | 227/175.1 |
| 6,346,111 B1 | 2/2002 | Gordon et al. | |
| 6,358,259 B1 | 3/2002 | Swain et al. | |
| 6,416,522 B1 * | 7/2002 | Strecker | 606/143 |
| 6,443,962 B1 | 9/2002 | Gaber | |
| 6,454,778 B2 | 9/2002 | Kortenbach | |
| 6,494,888 B1 | 12/2002 | Laufer et al. | |
| 6,500,195 B2 | 12/2002 | Bonutti | |
| 6,506,196 B1 | 1/2003 | Laufer | |
| 6,524,328 B2 | 2/2003 | Levinson | |
| 6,540,789 B1 | 4/2003 | Silverman et al. | |
| 6,558,400 B2 | 5/2003 | Deem et al. | |
| 6,572,629 B2 | 6/2003 | Kalloo et al. | |
| 6,663,639 B1 | 12/2003 | Laufer et al. | |
| 6,719,763 B2 | 4/2004 | Chung et al. | |
| 6,746,460 B2 | 6/2004 | Gannoe et al. | |
| 6,755,338 B2 * | 6/2004 | Hahnen et al. | 227/175.1 |
| 6,755,843 B2 | 6/2004 | Chung et al. | |
| 6,773,440 B2 | 8/2004 | Gannoe et al. | |
| 6,773,441 B1 | 8/2004 | Laufer et al. | |
| 6,821,858 B2 | 11/2004 | Namatame et al. | |
| 6,835,200 B2 | 12/2004 | Laufer et al. | |
| 6,869,395 B2 | 3/2005 | Page et al. | |
| 6,908,427 B2 | 6/2005 | Fleener et al. | |
| 6,955,643 B2 | 10/2005 | Gellman et al. | |
| 7,147,650 B2 * | 12/2006 | Lee | 606/205 |
| 7,434,717 B2 * | 10/2008 | Shelton et al. | 227/176.1 |
| 2001/0023352 A1 | 9/2001 | Gordon et al. | |
| 2002/0107530 A1 | 8/2002 | Sauer et al. | |
| 2002/0193809 A1 | 12/2002 | Meade et al. | |
| 2003/0032967 A1 | 2/2003 | Park et al. | |
| 2003/0045900 A1 | 3/2003 | Hahnen et al. | |
| 2003/0083674 A1 | 5/2003 | Gibbens | |
| 2003/0109900 A1 | 6/2003 | Martinek | |
| 2003/0120265 A1 | 6/2003 | Deem et al. | |
| 2003/0120292 A1 | 6/2003 | Park et al. | |
| 2003/0171760 A1 | 9/2003 | Gambale | |
| 2003/0181924 A1 | 9/2003 | Yamamoto et al. | |
| 2003/0225312 A1 | 12/2003 | Suzuki et al. | |
| 2003/0229296 A1 | 12/2003 | Ishikawa et al. | |
| 2003/0233104 A1 | 12/2003 | Gellman et al. | |
| 2003/0233108 A1 | 12/2003 | Gellman et al. | |
| 2004/0002720 A1 | 1/2004 | Kortenbach et al. | |
| 2004/0006351 A1 | 1/2004 | Gannoe et al. | |
| 2004/0024386 A1 | 2/2004 | Deem et al. | |
| 2004/0034369 A1 | 2/2004 | Sauer et al. | |
| 2004/0059350 A1 | 3/2004 | Gordon et al. | |
| 2004/0082963 A1 | 4/2004 | Gannoe et al. | |
| 2004/0098050 A1 | 5/2004 | Foerster et al. | |
| 2004/0122452 A1 | 6/2004 | Deem et al. | |
| 2004/0122453 A1 | 6/2004 | Deem et al. | |
| 2004/0122473 A1 | 6/2004 | Ewers et al. | |
| 2004/0147958 A1 | 7/2004 | Lam et al. | |
| 2004/0162568 A1 | 8/2004 | Saadat et al. | |
| 2004/0193184 A1 | 9/2004 | Laufer et al. | |
| 2004/0194790 A1 | 10/2004 | Laufer et al. | |
| 2004/0210243 A1 | 10/2004 | Gannoe et al. | |
| 2004/0215058 A1 | 10/2004 | Zirps et al. | |
| 2005/0015101 A1 | 1/2005 | Gibbens et al. | |
| 2005/0033319 A1 | 2/2005 | Gambale et al. | |
| 2005/0055038 A1 | 3/2005 | Kelleher et al. | |
| 2005/0070921 A1 | 3/2005 | Ortiz et al. | |
| 2005/0070926 A1 | 3/2005 | Ortiz | |
| 2005/0070931 A1 | 3/2005 | Li et al. | |
| 2005/0070934 A1 | 3/2005 | Tanaka et al. | |
| 2005/0070935 A1 | 3/2005 | Ortiz | |
| 2005/0075653 A1 | 4/2005 | Saadat et al. | |
| 2005/0075654 A1 | 4/2005 | Kelleher | |
| 2005/0143760 A1 | 6/2005 | Imran | |
| 2005/0143762 A1 | 6/2005 | Paraschac et al. | |
| 2005/0149067 A1 | 7/2005 | Takemoto et al. | |
| 2005/0165419 A1 | 7/2005 | Sauer et al. | |
| 2005/0192599 A1 | 9/2005 | Demarais | |
| 2005/0192601 A1 | 9/2005 | Demarais | |
| 2005/0203488 A1 | 9/2005 | Michlitsch et al. | |

FOREIGN PATENT DOCUMENTS

| | | |
|---|---|---|
| WO | WO-95/19140 | 7/1995 |
| WO | WO-96/22055 | 7/1996 |
| WO | WO-00/61012 | 10/2000 |
| WO | WO-01/10312 | 2/2001 |
| WO | WO-01/66001 | 9/2001 |
| WO | WO-01/89393 | 11/2001 |
| WO | WO-02/096327 | 12/2002 |
| WO | WO 2004/021894 | 3/2004 |
| WO | WO 2005/034729 | 4/2005 |

* cited by examiner

SURGICAL STAPLER WITH A BENDABLE END EFFECTOR

FIELD OF THE INVENTION

The present invention is directed broadly toward devices for surgical procedures, and more particularly toward devices that deposit staples in a selectable pattern or shape.

BACKGROUND OF THE INVENTION

Endoscopic and laparoscopic surgical instruments are often preferred over traditional open surgical devices since the use of natural orifices (endoscopic) or smaller incisions (laparoscopic) tends to reduce the post-operative recovery time and complications. Consequently, significant development has gone into a range of endoscopic and laparoscopic surgical instruments that are suitable for precise placement of a distal end effector at a desired surgical site. These distal end effectors engage the tissue in a number of ways to achieve a diagnostic or therapeutic effect (e.g., grasper, cutter, staplers, clip applier, access device, drug/gene therapy delivery device, and energy device using ultrasound, RF, laser, etc.).

For example, surgical staplers are used in a variety of surgical procedures to attach tissues. Typically, staplers utilize a rigid end effector adapted to fit through a cannula for delivery to a tissue site to be stapled. In existing surgical staplers, a pair of jaws of the end effector grasp the tissue to be stapled. Staples contained in a cartridge jaw are driven into the grasped tissue and deformed to hold the tissue by impinging on the anvil jaw. The staples form a predetermined pattern (e.g., one or more lines of staples) based upon the configuration of the staples in the rigid cartridge jaw.

In some surgical procedures, the formation of a non linear pattern of staples tailored to a particular configuration can be advantageous. For example, certain gastric bypass procedures require a surgeon to make a gastric pouch in a curved shape. Using current endoscopic surgical staplers and cutters, creating the pouch typically utilizes 3 or 4 individual cutting and stapling steps. In most instances, an endoscopic stapler/cutter would be removed and reloaded after every cut to insert a new cartridge for stapling. Such repeated removal and insertion is time consuming and also increases the possibility of surgical complications. Use of a surgical stapler that has an articulation joint below the end effector or a rigid cartridge jaw adapted to drive a predetermined curvilinear pattern of staples can still be problematic since specific tailoring of a staple pattern according to the particular needs of a surgical procedure is sometimes limited by the rigid construction of the end effector and the need to deliver the end effector through a narrow delivery tube to the tissue site.

Accordingly, a need exists for improved devices and methods for stapling and/or cutting tissue.

SUMMARY OF THE INVENTION

The present invention generally provides methods and devices for forming a pattern of staples that conform to a selected shape of a surgical stapler end effector. In one embodiment, a surgical stapler can include a handle connected to a proximal end of an elongate housing and a selectively bendable end effector coupled to the distal end of the housing. The end effector can include a first jaw having a supply of staples and a second jaw coupled to the first jaw. The end effector can also have a selected shape, and can be adapted to drive staples through tissue grasped between the jaws in a pattern conforming to the selected shape. In another embodiment, a surgical stapler can include a handle connected to a proximal end of an elongate connector, and two jaws coupled to the distal end of the connector. The jaw can be coupled together for grasping tissue. At least one of the jaws can be adapted to carry a supply of staples. Each jaw can be independently bent to a selected shape. The jaws can be adapted to fit in an access port when having a linear configuration. The jaws can also be adapted to be bendable when emerging from the access port.

In an exemplary embodiment, the end effector can be adapted to drive staples in a linear pattern when the selected shape of the end effector is a substantially linear configuration. The end effector can also drive staples in a non-linear pattern when the selected shape of the end effector is a substantially non-linear configuration. End effectors can also be adapted to be more flexible in at least one direction relative to another. Alternatively, or in addition, an end effector can be adapted to be selectively bendable in at least two directions. Some embodiments utilize an end effector that can be adapted to include an elastic material for biasing the end effector into a predetermined shape. In one example, the predetermined shape is a linear configuration.

One or more jaw flexing members can be coupled to a distal portion of an end effector in some embodiments. The jaw flexing member can be adapted to bend the end effector when the member is in tension. In a particular example, two or more jaw flexing members can be utilized, a distal portion of each jaw of the end effector being coupled to one jaw flexing member. Also, one or more flexing guides can be coupled to the end effector to hold a flexing member adjacent to the end effector. Some embodiments can also include at least one distal rigidizing element that can be adapted to be removably coupled to distal ends of each jaw of the end effector. The distal rigidizing element can hinder bending of a distal portion of a jaw. Embodiments can also include one or more driver elements that can be disposed with in at least a portion of an elongate housing. Driver elements can be adapted to move along a selected shape of the end effector to deploy staples therefrom. Further embodiments include one or more staple closing elements that can be moveably disposed within at least a portion of an elongate housing, and which can be adapted to move along the selected shape of the end effector to deform staples. Other embodiments include a blade element moveably disposed within at least a portion of an elongate housing. The blade element can be adapted to move along a portion of the end effector for cutting stapled tissue.

Another embodiment is directed to a surgical staple supply. The staple supply can have a selectively bendable base for conforming to the shape of a jaw of a surgical stapler. Deformable teeth can be coupled to, and extend from, the base. The deformable teeth can be adapted to pierce tissue. The base can also be adapted to include elastic material for biasing the base into a predetermined configuration.

A method for stapling tissue is encompassed in another embodiment. The method includes conforming the jaws of a surgical stapler's end effector into a selected shape, one of the jaws having a staples disposed within the jaw. The jaws are approximated to grasp tissue. Staples are subsequently driven from a jaw into the tissue. The driven staples are then deformed to effect closure on the tissue. Each jaw of the end effector can be bent in an independent desired shape. Staples can be deployed in the tissue to form a selected non linear pattern. The staples can also be deformed by bending the teeth of the driven staples.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles, structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with features of other embodiments. Such modifications and variations are intended to be included within the scope of the present invention.

In general, a surgical stapler is provided having a selectively bendable end effector that includes a first jaw and a second jaw coupled together to grasp tissue. The first jaw can include a supply of staples for stapling the grasped tissue. The end effector can have a selectable shape such that staples are driven into the grasped tissue in a pattern conforming to the selected shape of the end effector. For example, an end effector can be adapted to drive staples in a linear pattern when the selected shape of the end effector holds staples in a linear configuration (e.g., when the end effector is in a substantially linear configuration). As well, the end effector can be adapted to drive staples in a non linear pattern when the shape of the end effector holds the staples in a non linear configuration (e.g., when the end effector is in a substantially non linear configuration).

Figure 1:
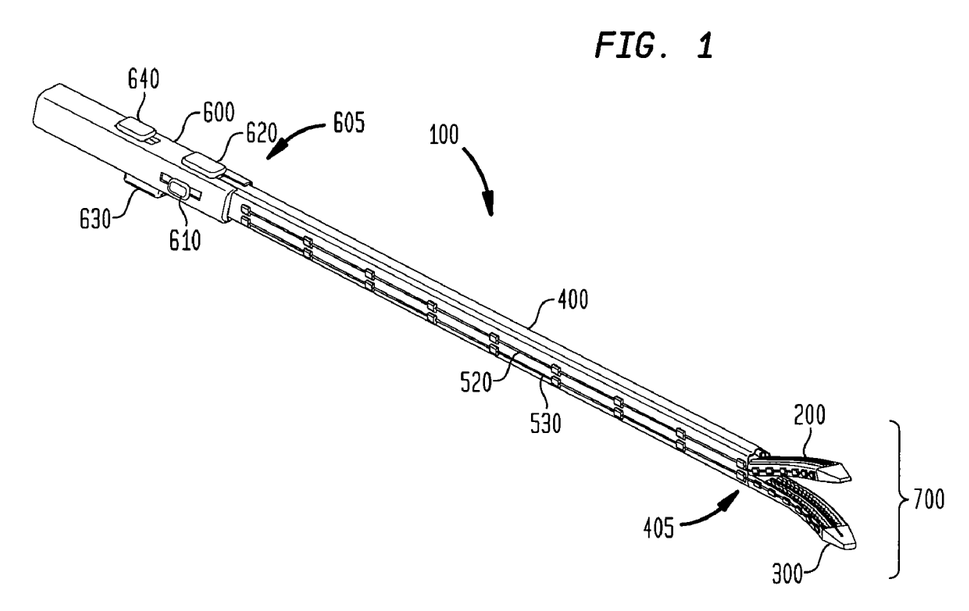
FIG. 1 is a perspective view of a surgical stapler in accord with an embodiment of the invention.

FIG. 1 illustrates an exemplary embodiment of a surgical stapler 100 having a pair of jaws 200, 300 that can each be independently bent into a selected shape. The surgical stapler 100 includes a handle 600 coupled to an elongate housing 400 extending from the handle's distal end 605. An end effector 700, which includes a pair of jaws 200, 300, is coupled to the distal end 405 of the elongate housing. One jaw 300 can be adapted to carry a supply of staples that are utilized by the surgical stapler 100. Jaw flexing elements 520, 530 can each be coupled at a proximal end to a control element 610 on the handle 600, and at a distal end to a jaw 200, 300 of the end effector 700. In use, the elongate housing 400 and end effector 700 are inserted into a patient, e.g., through an access port such as a delivery tube or cannula. The end effector can be configured in a closed or approximated position such that its cross sectional area is small enough to fit within the access port (e.g., the jaws can be arranged in a linear configuration). Upon emerging from the distal end of the access port, control element 610 can be moved to impart tension on the jaw flexing elements 520, 530 to cause each corresponding jaw 200, 300 to bend to a selected shape based upon the position of the control element 610. Though the embodiment of FIG. 1 shows an elongate housing 400 in a straight configuration, the housing 400 can also take other shapes, and/or can be bendable to facilitate the delivery of an end effector to a particular location in a patient. The elongate housing can utilize a number of different configurations (e.g., the housing have openings along its length and not be an enclosed structure). In general, an elongate connector can be used to couple an end effector to a handle, the elongate housing being one embodiment of an elongate connector. Also as shown in FIG. 1, the handle can also include other control elements 620, 630, 640 for operating other portions of the surgical stapler and end effector as described in more detail herein. While control elements 610, 620, 630, 640 are illustrated to be slider bars, the handle 600 can additionally or alternatively include other mechanisms, such as a rotatable knob, lever, sliding knob, etc. for operating the surgical stapler 100. A person skilled in the art will appreciate that the device can include a variety of other features not disclosed herein. For example, the device can include an articulation joint formed between the elongate housing 400 and the end effector 700 for allowing angular movement of the end effector 700 relative to the elongate housing 400. A trigger or other mechanism can be provided on the handle for angularly adjusting the end effector 700. In addition or alternatively, a joint can be present to allow rotation of the end effector 700, or the housing 400 and the end effector 700, about the longitudinal axis of the device 100.

The end effector 700 is described in greater detail with reference to the perspective view of the distal end of the stapler 100 shown in FIGS. 2 and 3 and the exploded view in FIG. 4A, the latter view omitting the elongate housing 400 for clarity. The staple holding jaw 300 can include an outer housing 310 with a slot 312 centered therein. The housing 310 can contain flexible spine elements 320, staple supports 340, and staple supplies 330. The pair of flexible spine elements 320 can be positioned toward the center of the outer housing 310 with the slot 312 passing therebetween. Staple supports 340 can be oriented in the outer housing 310 such that two staple supplies 330 are interlaced within the slots of the staple support 340. By way of example, a staple support 340 and two lines of staple supplies 330 can be positioned on each side of the outer housing 310. The end effector can be adapted to allow staples or staples supplies to be reloaded multiple times in the device (e.g., multiple usage of the stapler can be accomplished by allowing the staple supports 340 and the staple supplies 330 to be removably coupled to the staple holding jaw 300 so that other staple supplies can be loaded into the staple holding jaw 300). The opposing jaw 200 can include an outer housing 210. The jaws 200, 300 can be coupled to the distal end of elongate housing 400, and can be adapted to allow relative pivoting motion such that they are able to approximate (i.e., close) and distract (i.e., open). The distal end of each jaw 200, 300 can be adapted to accept a selectively removable distal rigidizing element 250, 350. Each jaw 200, 300 can be coupled to a jaw flexing member 520, 530, shown here for exemplary purposes as a cable, at a distal end 270, 370 of the jaw. Each jaw 200, 300 can also include one or more flexing guides 260, 360 through which a corresponding jaw flexing member 520, 530 is threaded.

Figure 5:
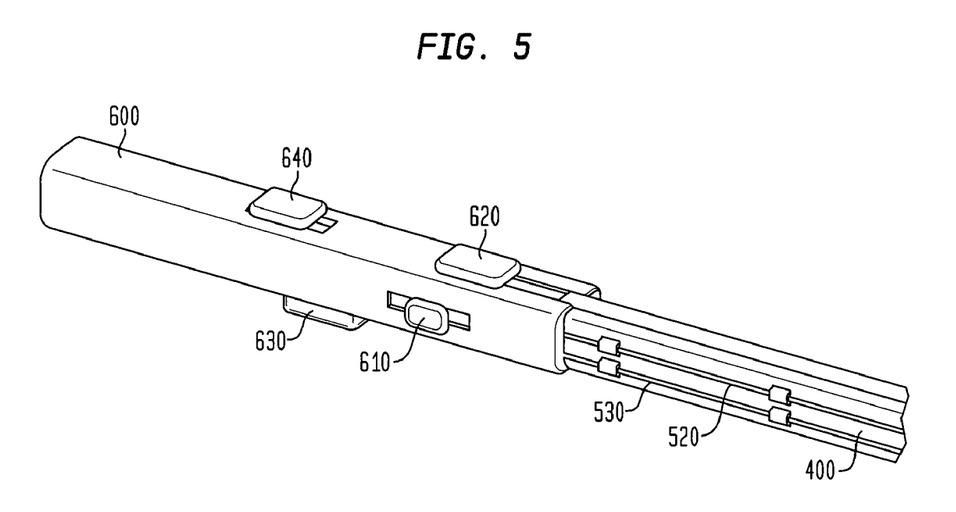
FIG. 5 is a perspective view of the handle and distal end of the elongate housing for the surgical stapler of FIG. 1.
Figure 6:
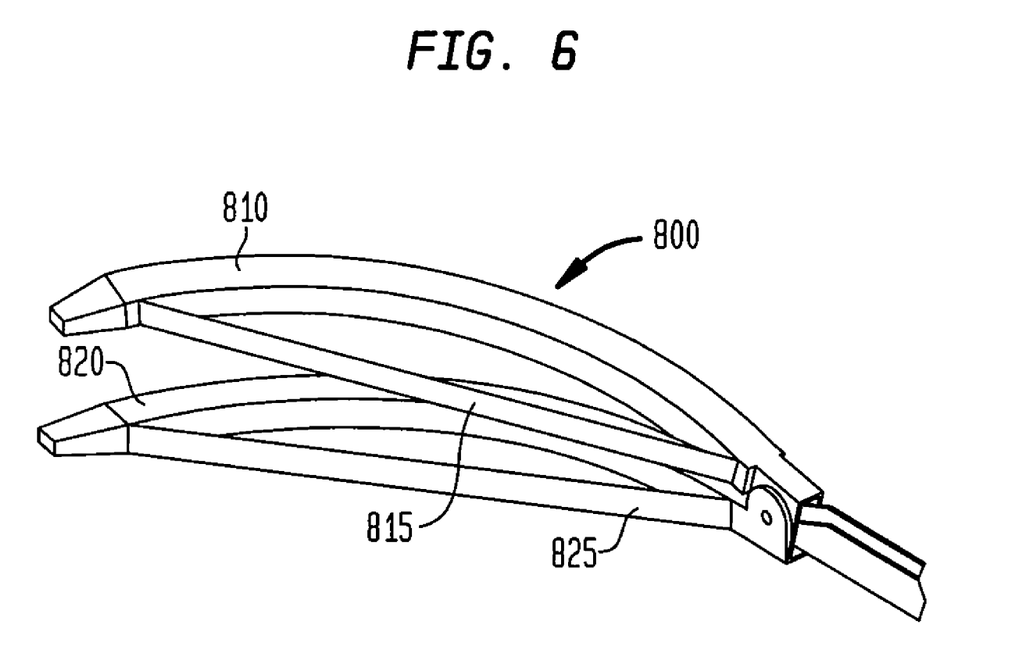
FIG. 6 is a perspective view of an alternate embodiment of an end effector for a surgical stapler, consistent with an embodiment of the invention.

In an exemplary embodiment, independent bending of each jaw of an end effector into a selected shape can be effected by applying tension to a corresponding jaw flexing element. With reference to FIGS. 2 and 3, since each jaw flexing member 520, 530 is coupled to the distal end of the corresponding jaw 200, 300, pulling on a member 520, 530 tends to effect bending of the jaw 200, 300. As a jaw flexing member is further tensioned, the corresponding jaw bends further in response to the additional force imparted to the distal end of the jaw by the jaw flexing member. In particular embodiments, a jaw can be selectively bent such that it is oriented at an angle up to about 45 degrees, or up to about 90 degrees, relative to a longitudinal axis of device 100 when the device 100 is oriented in a linear configuration. Alternative arrangements of the jaw flexing elements and end effector can provide further functionality. Though coordinated jaw bending can be effected by using a single control element 610 of a handle 600 that is coupled to both cables 520, 530 as shown in FIG. 5, two control elements can be also be implemented on a handle to provide independent means to apply tension to each cable respectively to allow independent selection of jaw shape. In addition, end effectors can be adapted to bend in more than one direction. For example, jaw flexing elements can also be implemented on the opposite side of the end effector 700 from where the cables 520, 530 are located to allow the end effector 700 to bend in an opposite direction relative to the adapted bending direction shown in FIGS. 2 and 3. Thus, embodiments can include an end effector adapted to be selectively bendable in at least one plane (i.e., in two directions). Though the embodiment shown in FIGS. 2 and 3 utilizes cables as jaw flexing elements, one skilled in the art will appreciate that other types of structures can also be used to impart a force on a jaw or end effector to cause bending. For example, FIG. 6 depicts the jaws 810, 820 of an end effector 800 being bent by jaw flexing elements 815, 825 that are embodied as flexible straps. As well, jaw flexing elements can be rigid structures, such as a rod, that can be coupled to the distal end of jaws by a hinge. An axial force acting pulling on a rod can cause the coupled jaw to bow away from the rod, the jaw forming a selected shape depending upon the magnitude of the axial force.

Figure 2:
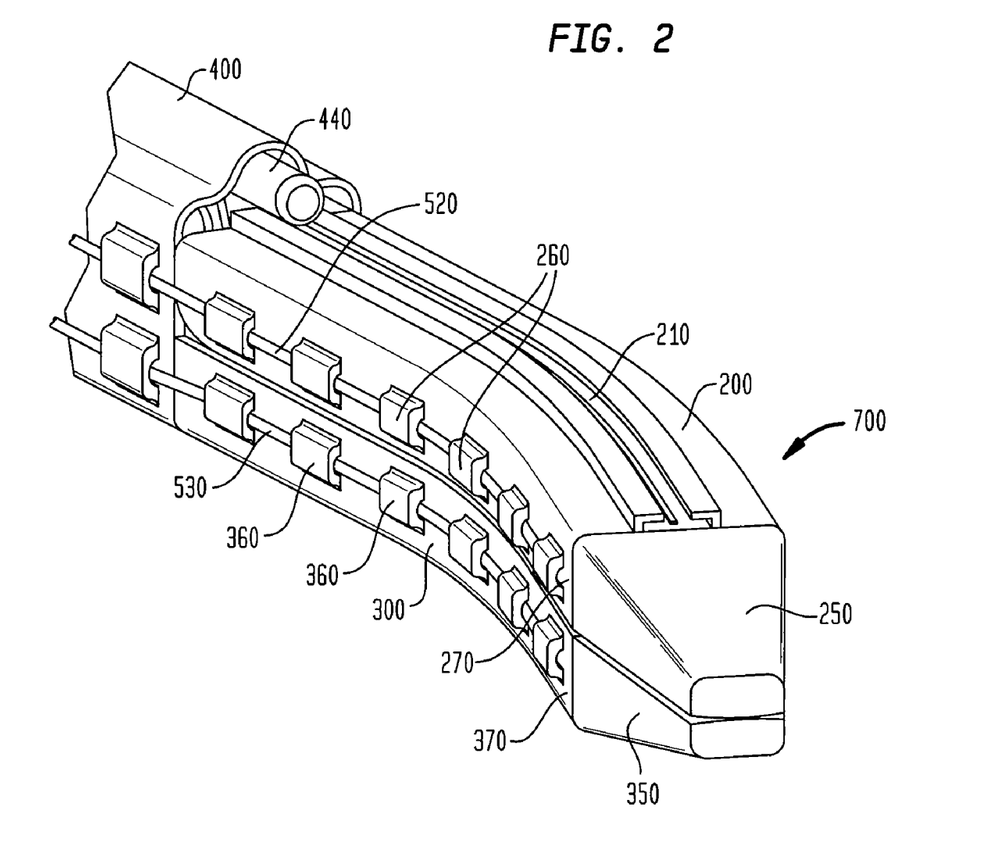
FIG. 2 is a perspective view depicting the jaws of the end effector of the surgical stapler of FIG. 1 with the jaws in a closed position.
Figure 3:
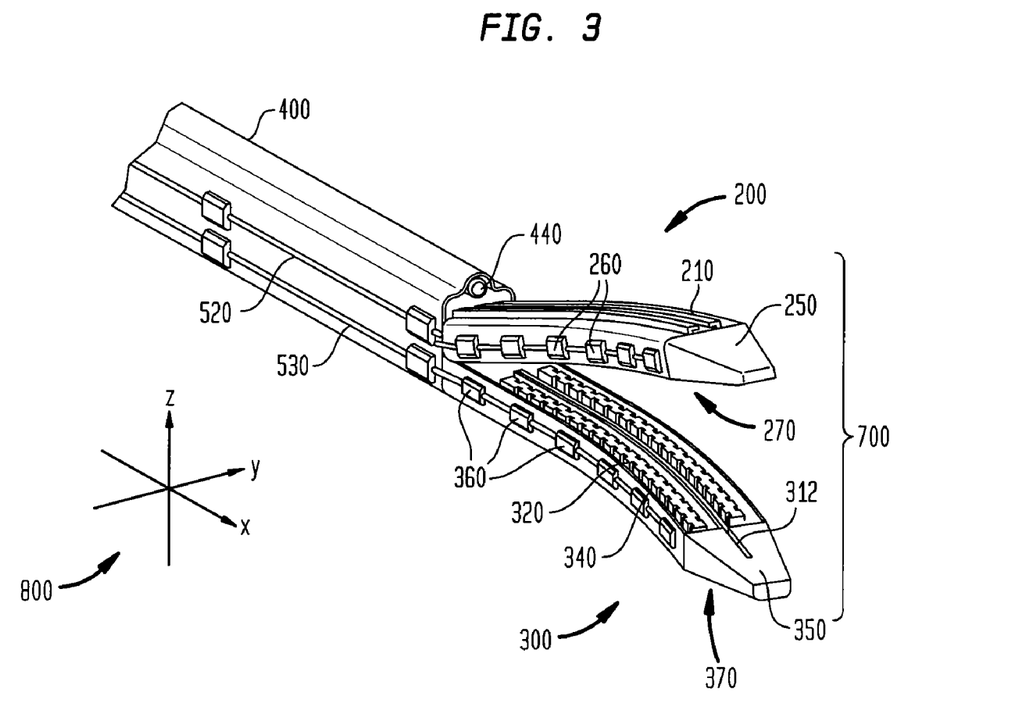
FIG. 3 is a perspective view depicting a set of coordinate axes and the jaws of the end effector of the surgical stapler of FIG. 1 with the jaws in an open position.
Figure 4A:
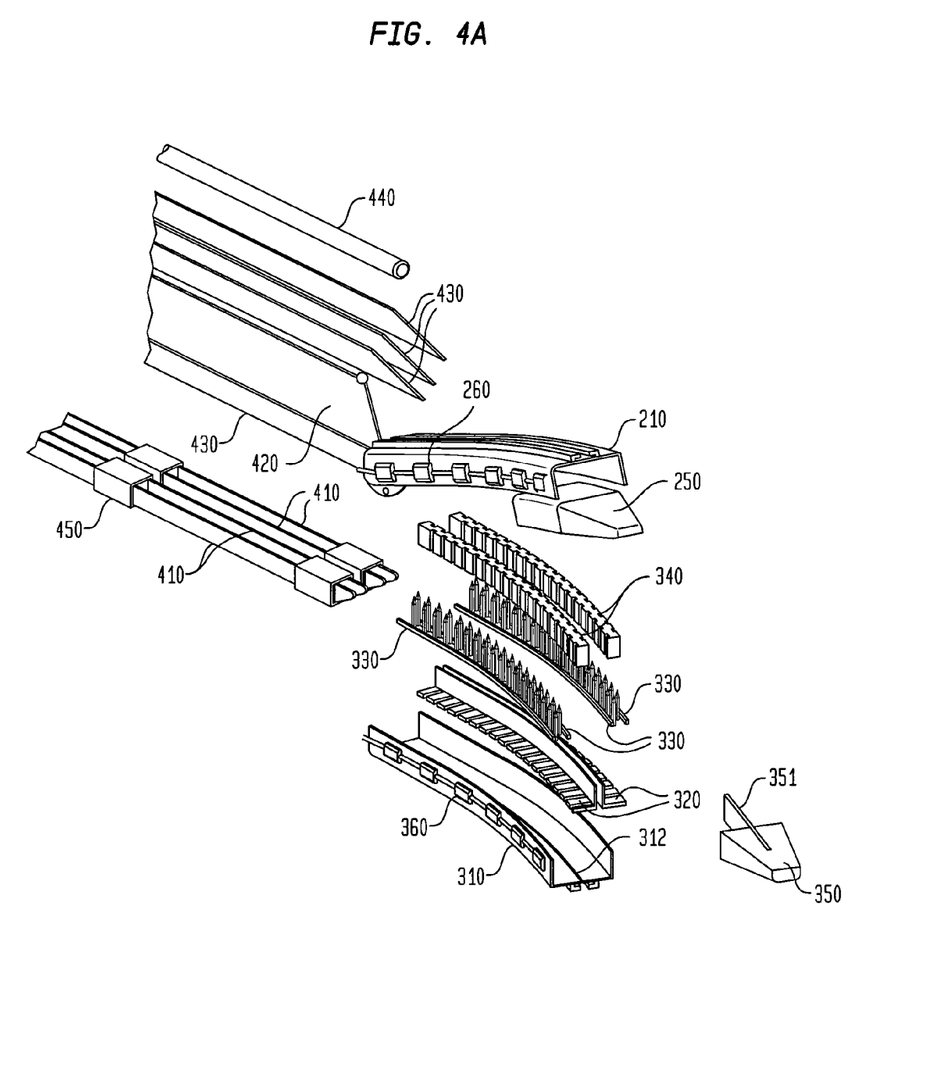
FIG. 4A is an exploded view of the distal end of the surgical stapler of FIG. 1 without showing the elongate housing.

As shown in FIGS. 2 and 3, flexing guides 260, 360 can be coupled to each jaw 200, 300 for holding a corresponding jaw flexing element 520, 530 adjacent to the end effector. With reference to the staple holding jaw 300, as a flexing cable 530 is pulled and tensed, the cable 530 tends toward a straight, taut configuration while the jaw 300 tends to bend and bow away from the cable 530. By threading the cable 530 through one or more flexing guides 360, the cable 530 can be constrained to a position adjacent to the jaw 300. This can be advantageous when the end effector is utilized in a small cavity area or if the end effector is delivered through an access port with substantial curvature to help maintain a limited cross section for the end effector. In another aspect, the positioning and number of flexing guides can be adapted to alter the selectable shape that a jaw may have. For example, use of several closely spaced flexing guides in a particular section of a jaw will tend to make that jaw section more rigid relative to other sections that have flexing guides spaced further apart. Thus the selected shape can have a varying radius of curvature. Clearly, however, the use of flexing guides is optional. For example, as shown in FIG. 6, the end effector 800 is bent to a selected shape without the use of flexing guides.

An end effector can be adapted with an elastic material such that the end effector is biased to conform to a predefined shape. Use of materials having elastic properties, such as spring steel, can impart a preferred shape to the end effector while allowing the end effector to deform when subjected to certain forces and to return to the preferred shape upon removal of the force. With reference to FIGS. 2 and 3, the jaws 200, 300 can have a selected bent shape when the cables 520, 530 are in tension. When the cables 520, 530 have little or no tension, however, the jaws 200, 300 tend to assume their normal configuration, forming a substantially straight shape. In particular, when the staple carrying jaw 300 forms a straight shape, the staples in the jaw 300 are aligned in a linear configuration. Thus, a stapler can deploy a linear pattern of staples or a non-linear pattern of staples that follows the selected shape of the end effector. One skilled in the art will appreciate that an end effector can be adapted to be biased toward other predetermined shapes, such as a curve with a particular curvature, and that staples in the end effector can also be arranged in various desired configurations when the end effector has a particular predetermined shape.

Figure 4B:
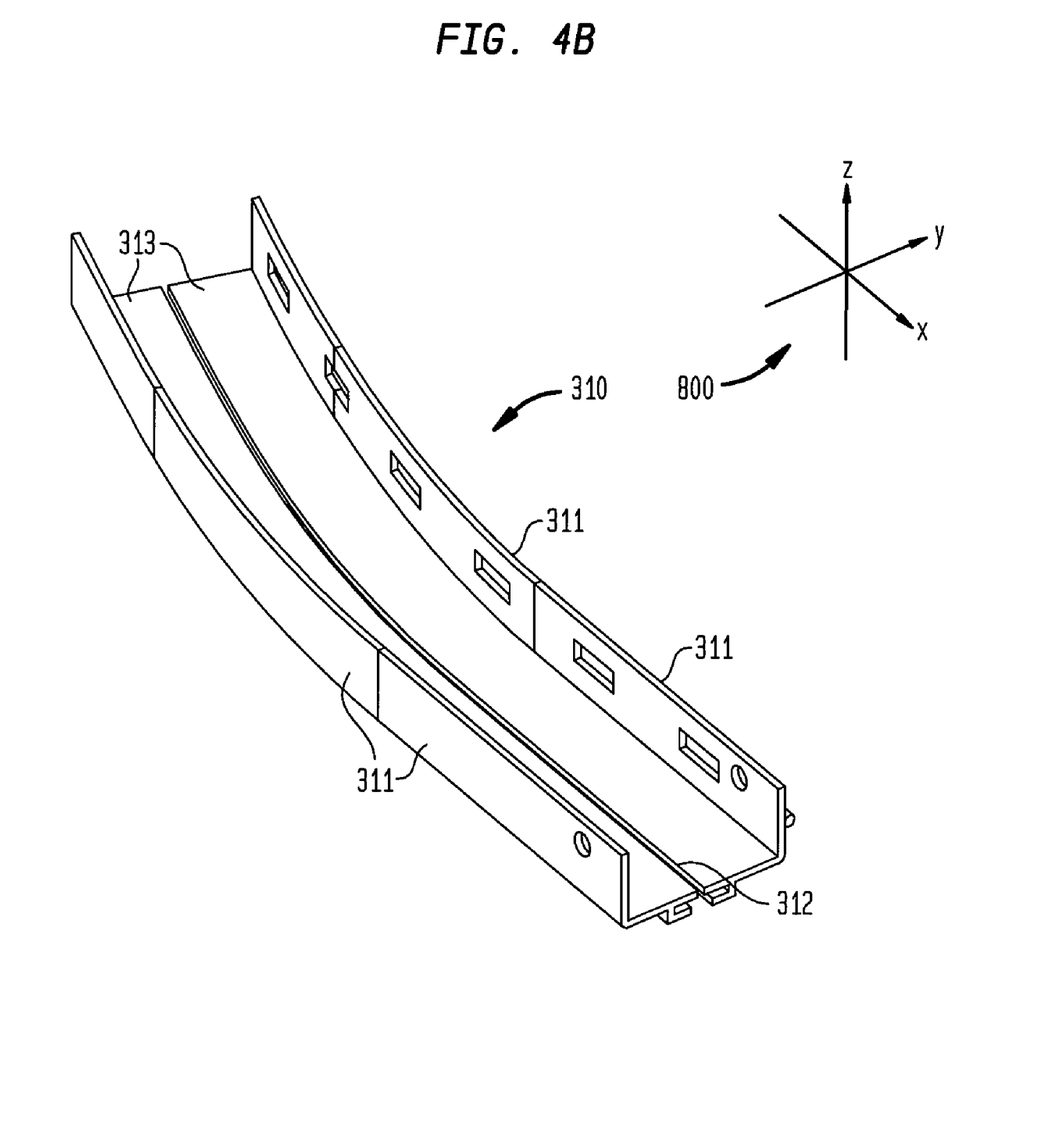
FIG. 4B is a close up perspective view of the outer housing of the staple carrying jaw shown in FIG. 4A.

In some embodiments, the end effector can be adapted to be more flexible in one direction than in another. For example, with reference to the coordinate axes 800 depicted in FIG. 3, the end effector 700 can be adapted to bend in a particular direction in the x-y plane, while being stiff enough in the x-z plane to allow staples to be driven. In general, an end effector can be made bendable through a combination of the types of material utilized, the shapes of the parts of the end effector, and the orientation of the parts relative to the forces acting on the parts. For example, as shown in FIG. 4B, outer housing 310 of the staple holding jaw 300 can include two plastic strips 313 that act as the base of the outer housing 310, each plastic strip 313 being flexible in the y-direction as indicated by axes 800. In an exemplary embodiment, the sides of the housing 310 can be made of thin metal strips 311 (e.g., small sheet sections of spring steel) that can be insert molded into the plastic strips 313. Each thin metal strip 311 can have a shape and orientation such that the y-dimension is substantially thinner than the z-dimension. The thin dimension of the sheet 311 in the y direction (approximately 1 mm) can allow the sheets to be flexible in the y-direction. Higher relative stiffness in the z-direction can be achieved by the relatively larger thickness in the z direction (approximately 6 mm), thus giving an end effector a preferred flexible direction in some embodiments. The elasticity of spring steel can also allow the end effector to have a preferred shape, i.e., a biased predefined shape that can be bent to a selected shape by applying a force, but which returns to the predefined shape when the force is relieved. The other structures of both jaws (e.g., upper jaw housing, flexible spine elements, staple supplies, staple supports, flexing guides, etc.) can be similarly constructed to impart similar directionally preferred flexibility or stiffness.

Figure 7:
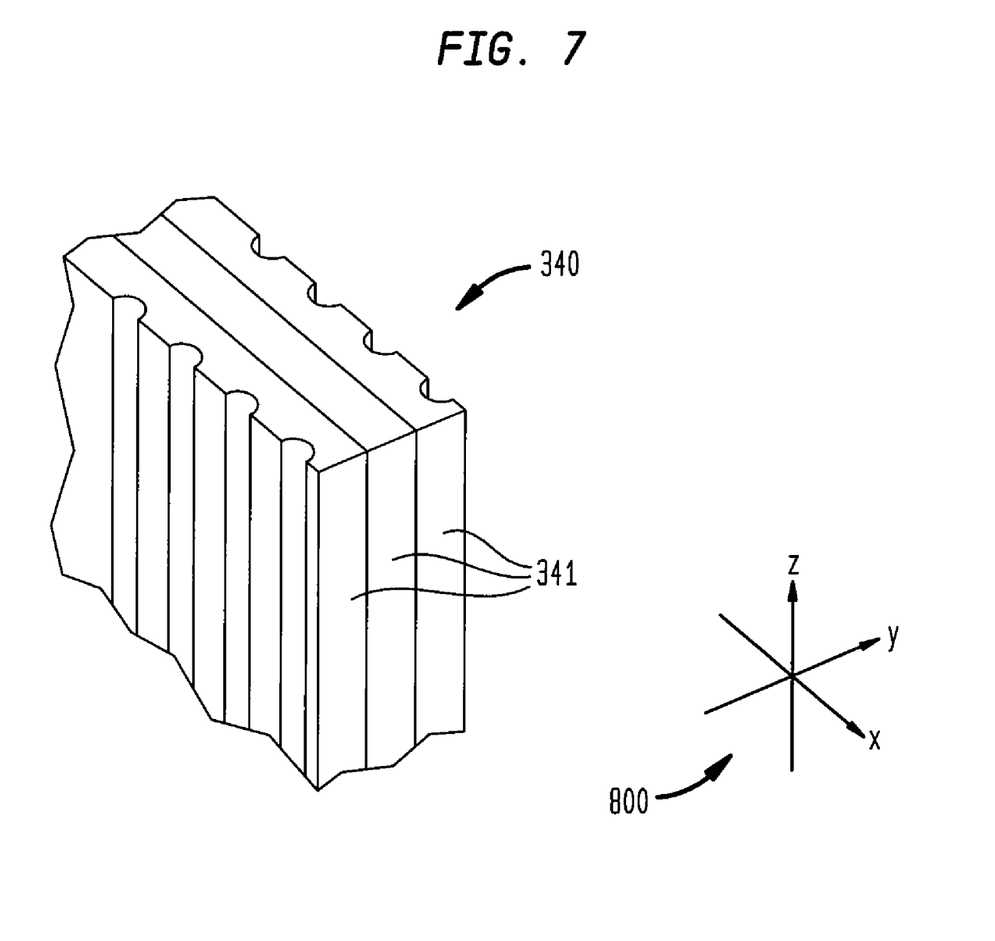
FIG. 7 is a perspective view of a section of a staple support that includes sheet of metal, consistent with an embodiment of the invention.

When a particular structure has a substantial width in the y-direction, two or more sheets of material can be layered together to provide the flexibility in the x-y plane and rigidity in the x-z plane. The sheets can be oriented such that the planar surfaces are parallel to the x-z plane, with the sheet thickness dimension perpendicular to the y-axis. For example, as depicted in FIG. 7, a staple support 340 is constructed of sheets 341 of spring steel assembled side by side. Allowing some relative movement between the sheets 341 can allow the sheets to flex when a force is applied in the y-direction. The concept of orienting sheets, or a plurality of sheets, to make structures for the surgical stapler can also be applied the driver elements 430 and the staple closing elements 410 that drive and deform staples, respectively, in a pattern conforming with the selectable shape of the end effector, as discussed in more detail herein. Beyond the concepts described previously, particular structures, such as the flexible spine elements 320, can also, or alternatively, utilize spacings or gaps between strips of materials to allow structural flexibility in a desired dimension. Though the embodiment discussed herein refers to the use of spring steel sheets and flexible plastic materials, one skilled in the art will readily acknowledge that other materials having adequate properties can be utilized. As well, a variety of other structure geometries can also be utilized in a bendable end effector (e.g., the base portions of the outer housing 313 could be constructed of thin strips of metal aligned along the elongate axis of the housing 313, the thin strips allowing the flexibility in the y-dimension). Indeed, the description of the construction of a flexible staple holding jaw herein can be applied to embodiments that generally include a staple holding cartridge that is selectively bendable.

Figure 8:
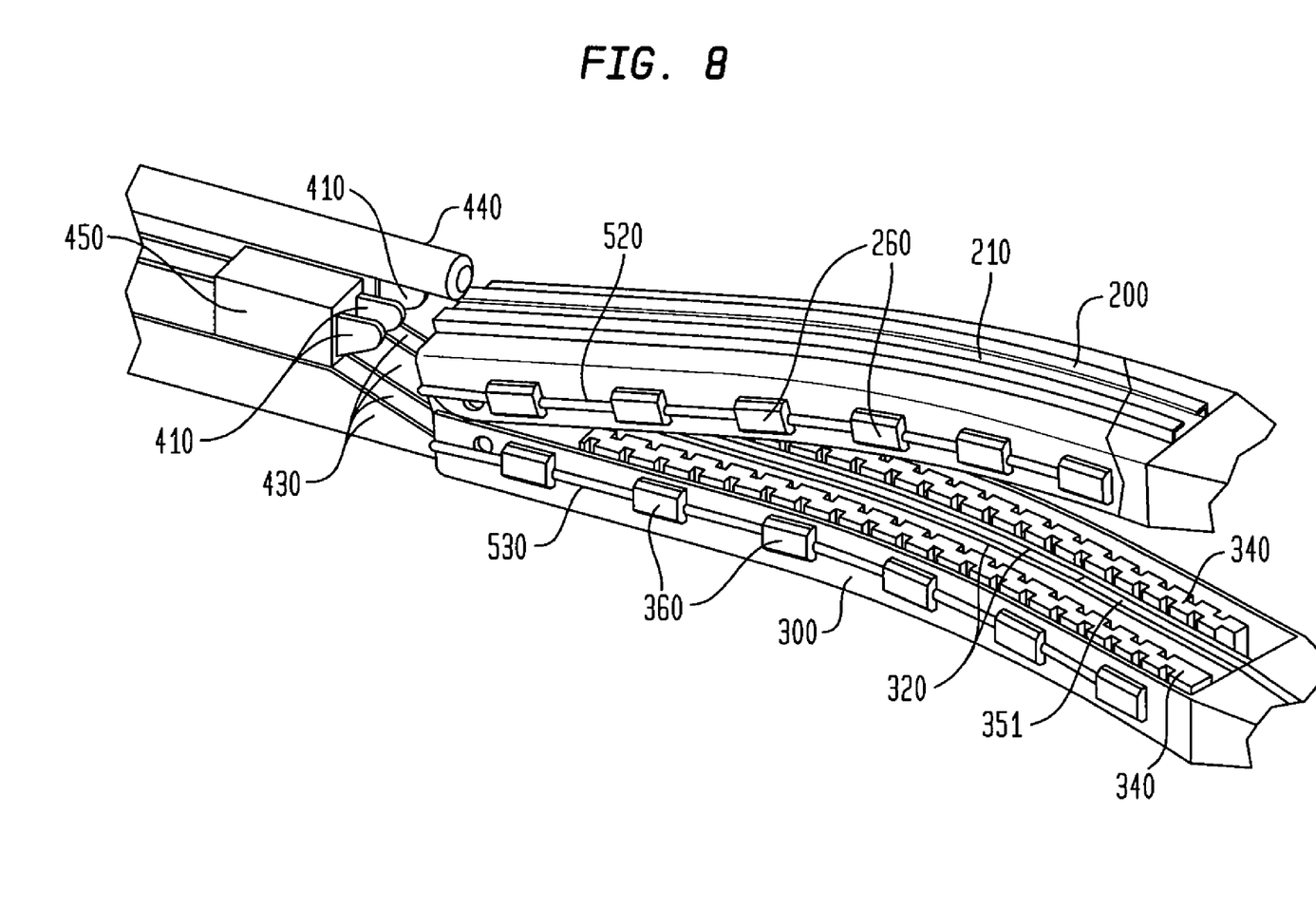
FIG. 8 is a close up perspective view of the proximal end of the end effector for the surgical stapler in FIG. 1 without showing the elongate housing.

End effector bending characteristics can be altered using rigidizing elements to hinder bending of a specific portion of a jaw or end effector. As depicted in FIGS. 3 and 4A, the distal end 270, 370 of each jaw can be adapted to accept a removable distal rigidizing element 250, 350. A distal rigidizing element 350 can include a rigid extension 351. As shown in FIG. 8, the extension 351 is adapted to straddle the distal ends of the flexible spine elements 320 in the lower jaw 300 within a distal region of the jaw of a slot 312. The rigid extension 351 hinders bending of the jaw 300 in a distal region corresponding to the length of the extension 351. Thus, the selected shape of a bendable jaw can be altered to have a different distribution of curvature depending upon the length of the rigid extension. Clearly, numerous distal rigidizing elements having varying extension lengths can be used to bend a jaw according to the needs of the staple operator. Furthermore, a distal rigidizing element need not utilize a rigid extension adapted to fit into a slot of a jaw. One skilled in the art will appreciate that distal rigidizing elements can be shaped and sized in various configuration to limit bending of a distal portion of a jaw. For example, a distal rigidizing element can utilize an extension that braces adjacent to one side of a distal portion of a jaw. Such an embodiment increase the rigidity of the distal portion of the jaw with respect to bending in the direction of the side having the extension, while not affecting the rigidity of the jaw in the opposite direction.

Other elements of the exemplary embodiment that are used to effect jaw closure of the end effector 700, and driving and deformation of staples are discussed with reference to FIGS. 4A, 5, and 8. Closure element 440 can be coupled at its proximal end to control element 620 (e.g., a button or other actuator) on handle 600. The closure element 440 emerges from the distal end of the housing 400 in the vicinity of the proximal end of the end effector 700. Driver elements 430 can be coupled to driver control element 630 on handle 600 at their proximal ends, and can also be disposed within at least a portion of the elongate housing 400. Each driver element 430 can have a wedge like shape at its distal end, and can be axially advanced into the end effector 700 to drive a staple supply 330. Staple closing elements 410 can be coupled at their proximal end to a control element 640 on handle 600. The staple closing elements 410 can be adapted to be disposed within, and emerge from, the elongate housing 400, and advanced through the end effector 700 to deform staples. Spacer block 450 can be used to maintain the relative spacing of the driver elements 430 and staple closing elements 410.

As briefly discussed earlier, opening and closing of the jaws 200, 300 can be effected using the closure element 440. In one embodiment, the jaws 200, 300 can be adapted to tend toward a distracted position (as shown in FIG. 3) by a spring or other biasing mechanism (not shown). For example, forward sliding of control element 620 can result in the advancement of closure element 440 to impinge upon upper jaw 200, subsequently forcing the upper jaw 200 to approximate to meet staple holding jaw 300. As depicted in FIG. 2, the closure element 440 need not be advanced through the entire length of the jaw to effect jaw closure. Since the jaw closure mechanism can be independent of the mechanism for driving staples, tissue to be stapled can be grasped for a user determined period of time to allow "milking" of the tissue. Withdrawal of the closure element 440 can cause the jaws 200, 300 to revert to the open position. As is readily apparent, closure elements can utilize a variety of materials and configurations consistent with their use to force the jaws of an end effector toward one another. For example, the closure element need not be an integral solid body extending the length of the elongate housing 400; it can be embodied as a shorter elongate structure that is coupled at its proximal end to radially flexible but axially more rigid connector that extends through the elongate housing 400. As well, the jaws of an end effector need not be biased toward an open position. A separate mechanism can be used to actuate separation of the jaws. One skilled in the art will appreciate that a variety of alternate mechanisms can be used to effect jaw movement.

Staples for a surgical stapler can be provided in the form of a staple supply. In general, a staple supply can be embodied as a plurality of deformable teeth adapted to pierce tissue. The teeth are coupled to, and extend from, a bendable base that is adapted to conform to the shape of a jaw of an end effector. With reference to the exemplary embodiment shown in FIG. 9, a staple supply 330 has teeth 331 which can be attached to one side of a bendable base 332 in a train like pattern (i.e., the teeth are arranged in a linear or curvilinear pattern). In one embodiment, the teeth are constructed from wire cut stamped metal, having a length of about 5 mm and a width of about 0.5 mm, and the base has a thickness of about 0.5 mm. The deformable teeth can be constructed with any material that can be adapted to penetrate tissue and be deformed to allow staple closure. The bendable base can be adapted to have elasticity that biases the base into a predetermined configuration (e.g., through the use of an elastic material). For example, the base can have a preferred straight configuration that aligns with a preferred straight shape of the jaw of a bendable end effector. The staple supply base can then conform to the bending or relaxation of the end effector to a selected shape. The teeth and base of a staple supply can be constructed of the same material or different materials chosen to complement the functioning of the specific elements (e.g., stamped metal for the teeth and spring metal for the base). One skilled in the art will appreciate that staple supplies can be constructed in configurations differing from those depicted in FIG. 9. For example, staple supplies can utilize multiple parallel trains of the teeth that are interconnected, or the base can have a predetermined curvilinear shape.

Figure 9:
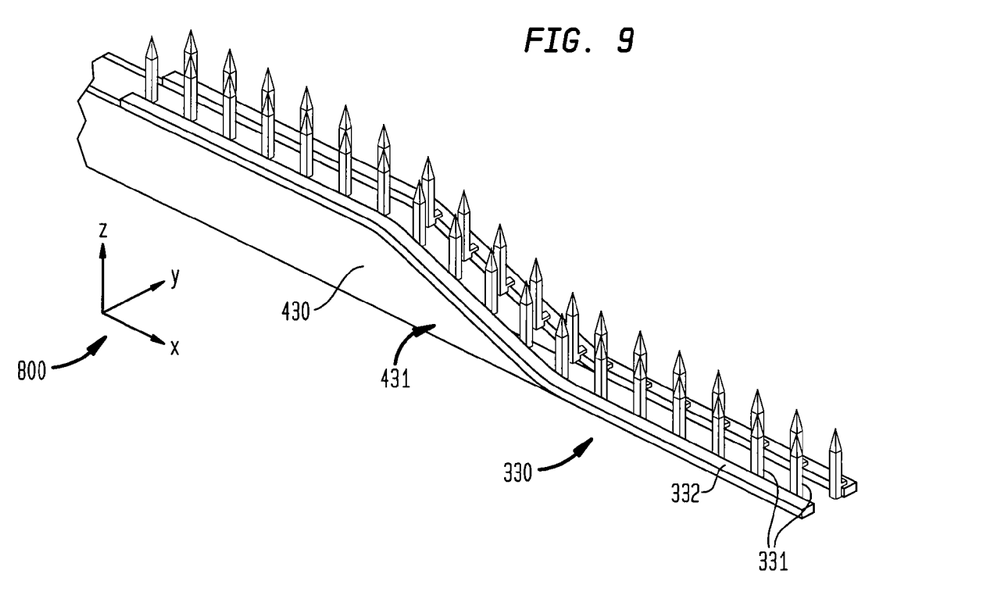
FIG. 9 is a perspective view of two staple supplies, each being driven by a corresponding driver element.

Driving of staples from end effector jaw into the tissue is described with reference to FIGS. 4A, 8, and 9 for the exemplary embodiment. Four sets of staple supplies 330 can be positioned in the notches of the two staple supports 340 that are located in the jaw 300. The staple supplies 330 are aligned such that the base of each staple supply is not covered by the staple support 340. Upon closure of the jaws 200, 300 on tissue, a driver element 430 having a wedge like distal portion 431 can be advanced into the lower jaw 300. The leading edge of the wedge 431 is adapted to slide under the base 332 of the staple supply 330. Thus, advancement of the driver element 430 forces the base to follow the surface shape of the driver element. The teeth 332, which are coupled to the side of the base, are forced up with the base to travel through the staple support 340 (see FIG. 10) and to pierce tissue. When multiple staple supplies are utilized, the driver elements can be coupled together to simultaneously or sequentially drive the staples according to a predefined scheme, or the driver elements can be independently advanced. With respect to the directional axes 800 depicted in FIG. 9, the driver element 430 is oriented such that its width (z-direction) is much larger than its depth (y-direction). Thus, the driver element 800 can bend in the y-direction to accommodate the selected shape of the end effector while maintaining enough stiffness in the z-direction to drive the staple supply 430. To the extent that other embodiments can utilize deeper dimensioned driver elements, layers of sheets can be sandwiched together to allow flexibility in the y-direction.

Figure 10:
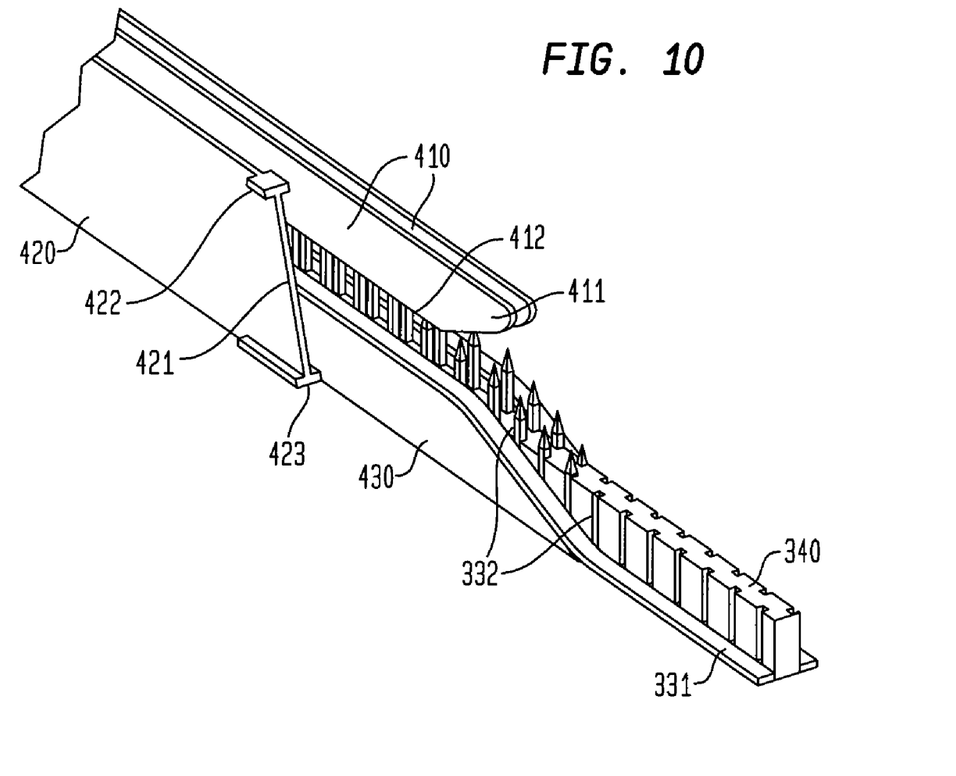
FIG. 10 is a perspective view of two staple supplies engaged with staple supports and an I beam knife, each staple supply being driven by a corresponding driver element and having teeth deformed by a corresponding staple closing element.

In one embodiment, staples that are driven into tissue are deformed to effect staple closure using staple closing elements 410, such as a wiper. With reference to FIGS. 8 and 10, after the teeth 332 of the staple supplies are driven into tissue, a staple closing element 410 can be advanced from the housing 400 into the end effector. The staple closing element 410 can have a wedge like shape 411 on its distal end, and can include a groove along its edge 412. Thus, as the staple closing element 410 is advanced, the groove along the edge 412 of the wedge 411 contacts the tip of the teeth and bends the tip in the plane of the staple closing element (i.e., horizontally) as shown in FIG. 10. Like the driver elements, the staple closing elements can have coupled movement according to a predefined sequence, or they can be advanced individually. Furthermore, the staple closing elements can also have a sheet like structure that allows them to flex to follow the selected shape of the end effector, while maintaining vertical (i.e., z-axis) rigidity to deform the staples.

In some embodiments, the movement of the driver elements and staple closing elements are independent from each one another. Other embodiments, however, may couple the movement of the driver elements and staple closing elements. One particular example is shown in FIG. 10, where the driver elements and staple closing elements can be advanced together with the driver elements leading staple closing elements by a predetermined distance and/or time. In another example, a driver element can have a distal portion configured as a first wedge shape up to an intermediate flat plateau, followed by a second wedge to a final plateau. Using such a configuration, a driver element and a staple closing element can be coupled such that the leading edge of the staple closing element is positioned even with the intermediate plateau region of the driver element. Upon advancement of the assembly, staple teeth can be driven through the tissue when rising due to the first wedge structure. The staple closing element then contacts the tips of the teeth to begin deformation. Further staple movement by the second driver wedge can then cause further deformation against the staple closing element to effect full staple closure.

Other embodiments can include other devices that can be used in conjunction with a surgical stapler during a laparoscopic or endoscopic procedure. For example, a surgical stapler can include a blade element such as a knife adapted to move along a portion of the end effector to cut stapled tissue. With reference to FIGS. 3 and 10, an I beam knife 420 can be coupled to a slider button (not shown) on the handle 600. Upon closure of the jaws 200, 300, the leading edge 421 can be advanced from the distal end of the elongate housing 400 into the end effector 700 through the slot 312 formed between the flexible spine elements 340 in the jaw 300. Slot 210 on the top jaw 200 and a corresponding slot on the bottom jaw 300 can be used to accommodate the gussets 422, 423 and thereby guide the movement of the knife 420 along the shape of the end effector. Since the gussets 422, 423 can securely engage the jaws 200, 300, advancement of the knife 420 can help secure closure of the jaws during staple formation. One skilled in the art will appreciate that a number of different knife structures, or other surgical devices can be used with a bendable end effector.

Exemplary methods for stapling tissue with a bendable end effector are also provided. In one exemplary embodiment, an end effector having a supply of staples is positioned at a tissue site to be stapled. If necessary, the end effector can be approximated by closing and aligning the jaws of the end effector to fit an access tube or cannula. Alternatively, the end effector can be endoscopically inserted into a natural orifice or laparoscopically through a small incision. Upon traveling through and emerging from a tube or other opening, the jaws of the end effector can be moved to an open, distracted position. The jaws of the end effector can each be bent to conform to a selected shape. Tissue to be stapled can then be grasped by the jaws. The jaws can optionally squeeze the tissue for a period of time to induce "milking" of the tissue. Staples can subsequently be driven from a staple containing jaw of the end effector into the tissue. Staple deformation can be performed on the driven staples to effect closure of the staples on the tissue (e.g., bending the teeth of the driven staples). The staples will be deployed into tissue in a pattern conforming to the selected shape of the end effector. For example, the staples can be deployed in a linear pattern or a non-linear pattern. As well, other patterns of staples can be formed such as staggered rows or curvilinear shapes. In other embodiments, the end effector can be selectively shaped in a one or more directions. Alternatively, or in addition, the selected shape can have a varying radius of curvature. The surgical stapler can also perform additional functions such as cutting tissue after the tissue has been stapled.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present invention. As well, one skilled in the art will appreciate further features and advantages of the invention based on the above-described embodiments. Accordingly, the invention is not to be limited by what has been particularly shown and described, except as indicated by the appended claims.

What is claimed is:

1. A surgical stapler, comprising:
    an elongate housing having a handle portion; and an end effector coupled to the distal end of the housing and including a first jaw having a supply of staples and a second jaw coupled to the first jaw, the end effector having an adjustable configuration to enable selection of a shape for driving staples through tissue grasped between the jaws in a pattern conforming to the selected shape, wherein the handle portion of the housing controls adjustment of the end effector to the selected shape.

2. The surgical stapler of claim 1, wherein the end effector is adapted to drive staples in a linear pattern when the selected shape of the end effector is in a substantially linear configuration, and in a non-linear pattern when the selected shape of the end effector is in a substantially non-linear configuration.

3. The surgical stapler of claim 1, wherein the end effector includes an elastic material effective to bias the end effector to a predetermined shape.

4. The surgical stapler of claim 3, wherein the predetermined shape is a linear configuration.

5. The surgical stapler of claim 1, wherein the end effector is adapted to be selectively bendable in at least one plane.

6. The surgical stapler of claim 1, further comprising:
at least one jaw flexing member coupled to a distal portion of the end effector and the handle portion, and adapted to bend the end effector when the at least one jaw flexing member is in tension.

7. The surgical stapler of claim 6, further comprising:
at least two jaw flexing members, a distal portion of each jaw of the end effector coupled to one jaw flexing member.

8. The surgical stapler of claim 6, further comprising:
at least one flexing guide coupled to the end effector for holding the at least one jaw flexing member adjacent to the end effector.

9. The surgical stapler of claim 1, further comprising:
at least one distal rigidizing element adapted to be removably coupled to a distal end of each jaw of the end effector, and effective to prevent bending of a distal portion of each jaw.

10. The surgical stapler of claim 1, further comprising:
at least one driver element movably disposed within at least a portion of the elongate housing and adapted to move along the selected shape of the end effector to deploy staples therefrom.

11. The surgical stapler of claim 1, further comprising:
at least one staple closing element movably disposed within at least a portion of the elongate housing, and adapted move along the selected shape of the end effector to deform staples.

12. The surgical stapler of claim 1, further comprising:
a blade element movably disposed within at least a portion of the elongate housing, and adapted to move along at least a portion of the end effector for cutting stapled tissue.

13. The surgical stapler of claim 1, wherein the supply of staples includes an elastic selectively bendable base adapted to conform to a shape of a jaw of a surgical stapler, and a plurality of deformable teeth extending from the base, the teeth being adapted to pierce tissue.

14. The surgical staple supply of claim 13, wherein the base is adapted to have elasticity for biasing the base into a predetermined configuration.

15. The surgical stapler of claim 1, wherein at least one of the first jaw and the second jaw is bendable into a selected shape by the handle portion in a first plane and is stiffer in at least one orthogonal plane relative to the first plane.

16. The surgical stapler of claim 15, wherein the end effector is adapted to drive staples a direction parallel with the at least one orthogonal plane.

17. A surgical stapler, comprising:
a handle;
an elongate connector coupled to the handle at a proximal end of the connector;
two jaws coupled to the distal end of the connector, the jaws movably coupled together for grasping tissue to be stapled, at least one jaw adapted to carry a supply of staples, at least one jaw having an adjustable configuration to enable selection of a shape for applying staples to tissue in the selected shape and being bendable into the selected shape by the handle in a first plane and being stiffer in at least one orthogonal plane relative to the first plane.

18. The surgical stapler of claim 17, wherein the jaws are adapted to fit in an access port when having a linear configuration, and to be bendable when emerging from the access port.

19. The surgical stapler of claim 17, wherein at least one jaw includes a staple holding cartridge that is selectively bendable into the selected shape.

20. The surgical stapler of claim 17, wherein the jaws are adapted to drive staples through tissue grasped between the jaws in a direction parallel with the at least one orthogonal plane.

* * * * *

UNITED STATES PATENT AND TRADEMARK OFFICE
CERTIFICATE OF CORRECTION

PATENT NO. : 7,651,017 B2
APPLICATION NO. : 11/287525
DATED : January 26, 2010
INVENTOR(S) : Ortiz et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 516 days.

Signed and Sealed this

Twenty-third Day of November, 2010

David J. Kappos
*Director of the United States Patent and Trademark Office*